(12) United States Patent
Crawford et al.

(10) Patent No.: US 8,906,695 B1
(45) Date of Patent: Dec. 9, 2014

(54) NANOSCALE SPINTRONIC CHEMICAL SENSOR

(71) Applicant: University of South Carolina, Columbia, SC (US)

(72) Inventors: Thomas M. Crawford, Irmo, SC (US); Samir Y. Garzon, Cayce, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 13/732,823

(22) Filed: Jan. 2, 2013

Related U.S. Application Data

(62) Division of application No. 12/442,951, filed as application No. PCT/US2007/081070 on Oct. 11, 2007, now Pat. No. 8,372,344.

(60) Provisional application No. 60/851,091, filed on Oct. 11, 2006.

(51) Int. Cl.
*G01N 15/06* (2006.01)
*G01N 33/00* (2006.01)
*G01N 33/48* (2006.01)

(52) U.S. Cl.
USPC .............. 436/151; 422/50; 422/83; 422/68.1; 422/82.01; 422/82.02; 422/98; 564/271; 365/173; 365/202; 365/171; 257/295; 436/43; 436/63; 436/149; 436/150; 436/173

(58) Field of Classification Search
CPC .......... G01N 27/3271; G01N 33/5438; G01N 27/126; G01N 33/0031
USPC ................ 422/50, 83, 68.1, 82.01, 82.02, 98; 564/271; 365/173, 202, 171; 257/295; 436/43, 63, 149, 150, 173
See application file for complete search history.

(56) References Cited

U.S. PATENT DOCUMENTS

| | | | |
|---|---|---|---|
| 4,529,621 A | 7/1985 | Ballard | |
| 4,978,938 A | 12/1990 | Partin et al. | |
| 5,445,008 A * | 8/1995 | Wachter et al. | 73/24.06 |
| 5,792,510 A * | 8/1998 | Farrow et al. | 427/130 |
| 6,262,306 B1 * | 7/2001 | Leriche et al. | 564/271 |
| 6,821,596 B2 | 11/2004 | Terao et al. | |
| 7,031,186 B2 | 4/2006 | Kang et al. | |
| 2004/0257894 A1 | 12/2004 | Onogi et al. | |
| 2005/0087000 A1 * | 4/2005 | Coehoorn et al. | 73/53.01 |
| 2005/0145909 A1 * | 7/2005 | Giebeler et al. | 257/295 |

(Continued)

OTHER PUBLICATIONS

International Search Report for PCT Application No. PCT/US07/81070 dated Oct. 3, 2008, 2 pages.

(Continued)

*Primary Examiner* — Brian J Sines
(74) *Attorney, Agent, or Firm* — Dority & Manning, P.A.

(57) ABSTRACT

In general, the present disclosure is directed toward a novel hybrid spintronic device for converting chemical absorption into a change in magnetoresistance. This device uses a novel magnetic material which depends on the attachment of an organic structure to a metallic film for its magnetism. Changes in the chemical environment lead to absorption on the surface of this organometallic bilayer and thus modify its magnetic properties. The change in magnetic properties, in turn, leads to a change in the resistance of a magnetoresistive structure or a spin transistor structure, allowing a standard electrical detection of the chemical change in the sensor surface.

10 Claims, 9 Drawing Sheets

(56) References Cited

U.S. PATENT DOCUMENTS

| | | |
|---|---|---|
| 2005/0147977 A1* | 7/2005 | Koo et al. .................. 435/6 |
| 2005/0238967 A1 | 10/2005 | Rogers et al. |
| 2005/0239948 A1 | 10/2005 | Haik et al. |
| 2005/0249667 A1 | 11/2005 | Tuszynski et al. |
| 2006/0003152 A1 | 1/2006 | Youngs |
| 2007/0202403 A1 | 8/2007 | Oh et al. |
| 2007/0237987 A1 | 10/2007 | Winarski |

OTHER PUBLICATIONS

International Search Report for PCT Application No. PCT/US07/80080 dated Sep. 22, 2008, 2 pages.

Gokemeijer, et al., "Recording head metrology at sub-100 nm device dimensions" Journal of Applied Physics, 2005. 97: p. 083912-1-083912-4.

Gokemeijer, et al. "Direct measurement of the field from a magnetic recording head using an InAs hall sensor on a contact write/read tester" Journal of Magnetism and Magnetic Materials, 2005. 290-291: p. 254-256.

Terris et al. "Nanofabricated and Self-Assembled Magnetic Structures as Data Storage Media" J. Phys. D: Appl. Phys. 38 (2005) R199-R222.

Gokemeijer, et al., "Write field measurements of a perpendicular head on a soft underlayer film" IEEE Transactions on Magnetics, 2006, 42: p. 163-165.

Shi et al., "A General Approach to Binary and Ternary Hybrid Nanocrystals" Nano Letters 2006, vol. 6, No. 4, p. 875-881.

Leonhardt, et al., "Comparison of perpendicular and longitudinal magnetic recording using a contact write/read tester" IEEE Trans, Magn., 2001. 37(4): p. 1580-1582.

Lohau, et al., "Dynamic coercivity measurements of antiferromagnetically coupled magnetic media layers" Appl. Phys. Lett., 2001. 78(18) p. 2748-2750.

Moser, et al., "Dynamic coercivity measurements in thin film recording media using a contact write/read tester" J. Appl. Phys., 1999. 85(8): p. 5018-5020.

Schrag, et al., "Submicron electrical current density imaging of embedded microstructures" Appl. Phys. Lett., 2003. 82(19) p. 3272-3274.

Yammamoto et al., "Scanning magnetoresistance microscopy (SMRM): Imaging with a MR head" J. Appl. Phys., 1997. 81(8): p. 4696-4698.

* cited by examiner

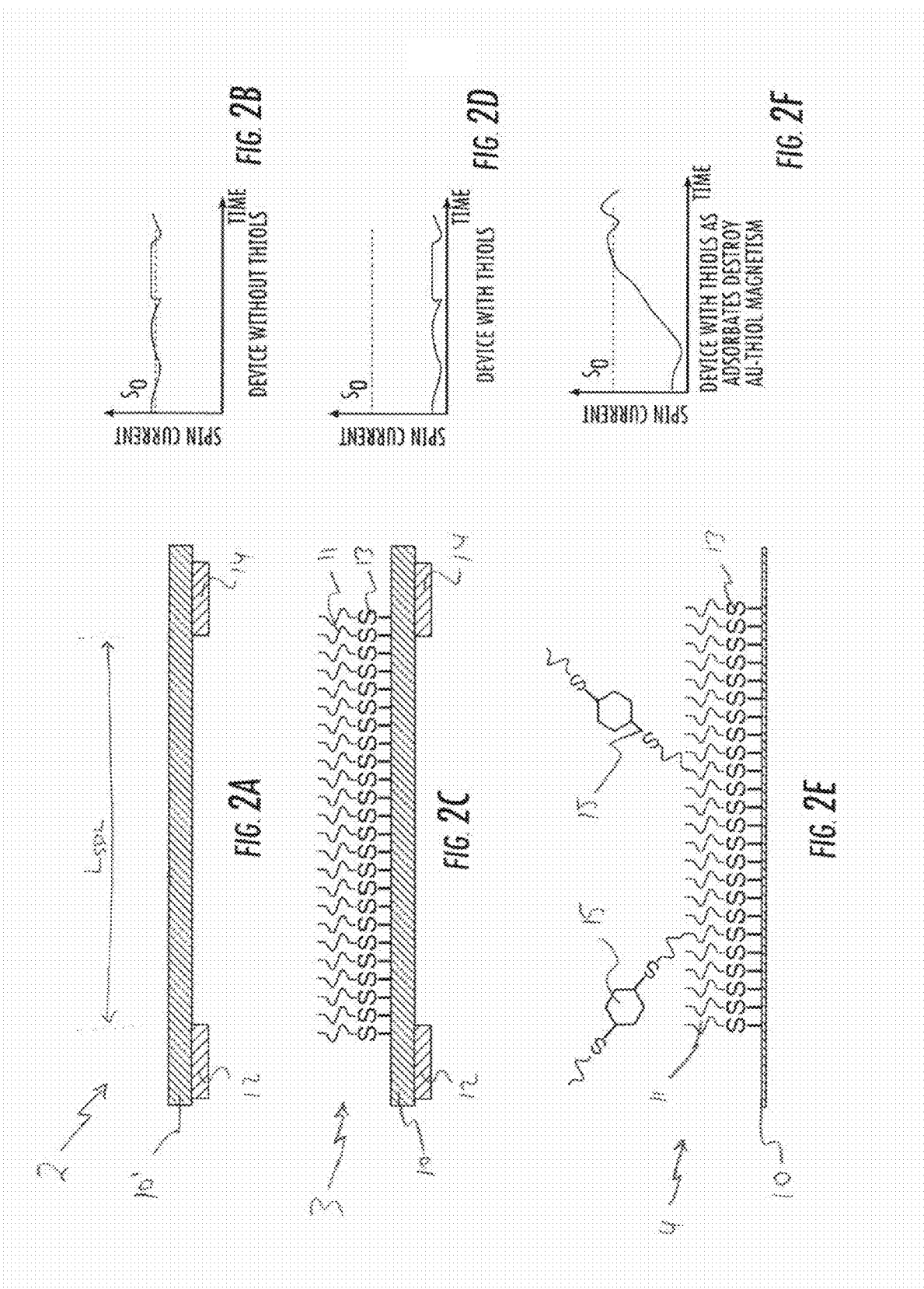

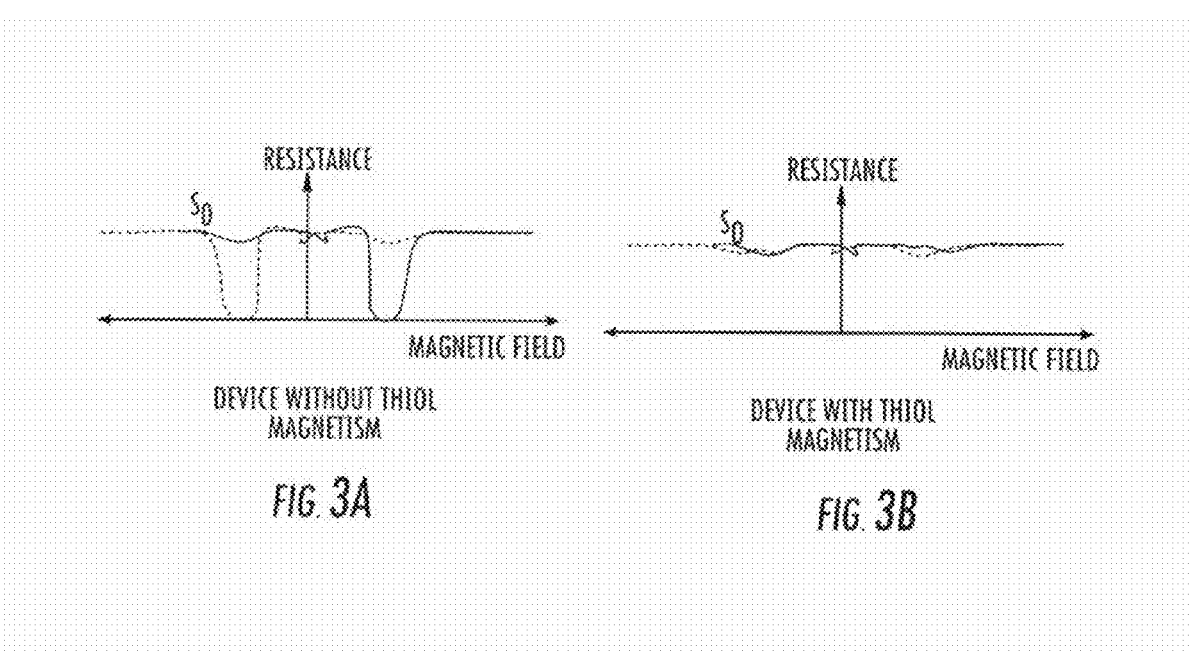

NANOSCALE SPINTRONIC CHEMICAL SENSOR

PRIORITY INFORMATION

This present application is a divisional of and claims priority to U.S. patent application Ser. No. 12/442,951 titled "Nanoscale Spintronic Chemical Sensor" of Crawford, et al. filed on Jan. 4, 2010, which is a nationalization phase application of International Application No. PCT/US2007/081070 filed on Oct. 11, 2007, and claims priority to the U.S. Provisional Patent Application No. 60/851,091 filed on Oct. 11, 2006, titled "Nanoscale Spintronic Chemical Sensor" of Crawford, et al., the disclosures of which are incorporated by reference herein.

BACKGROUND OF INVENTION

Chemical sensors which are lightweight, portable, and inexpensive are needed for anti-terrorism and environmental applications. Magnetoresistive sensors have found applications in magnetic data storage as well as in automotive and other process control sensing applications. However, converting chemical sensing into a magnetically detectable signal has not been reported. The ability to detect environmental contaminants through low-voltage, battery or solar-powered magnetoresistive sensors would be a major breakthrough in deploying such sensors in a variety of areas, as opposed to optical chemical sensing which requires both an optical source such as a laser (often intense for laser-induced breakdown spectroscopy) and a detector.

As such, a need exists for a low-voltage, battery or solar-powered magnetoresistive sensor having the ability to detect environmental contaminants.

SUMMARY OF INVENTION

Objects and advantages of the invention will be set forth in part in the following description, or may be obvious from the description, or may be learned through practice of the invention.

In general, the present disclosure is directed toward a novel hybrid spintronic device for converting chemical absorption into a change in magnetoresistance. This device uses a novel magnetic material which depends on the attachment of an organic structure to a metallic film for its magnetism. Changes in the chemical environment lead to absorption on the surface of this organometallic bilayer and thus modify its magnetic properties. The change in magnetic properties, in turn, leads to a change in the resistance of a magnetoresistive structure or a spin transistor structure, allowing a standard electrical detection of the chemical change in the sensor surface.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which:

FIGS. 2a-2c show three different embodiments of a device for sensing the presence of a chemical in the atmosphere. FIGS. 2d-2f show a plot of the spin current vs. time of the devices shown in FIGS. 2a-2c, respectively.

FIGS. 3a-3b show how the resistance of the devices in FIGS. 1-2 changes with an applied magnetic field.

Figures 1A, 1B:
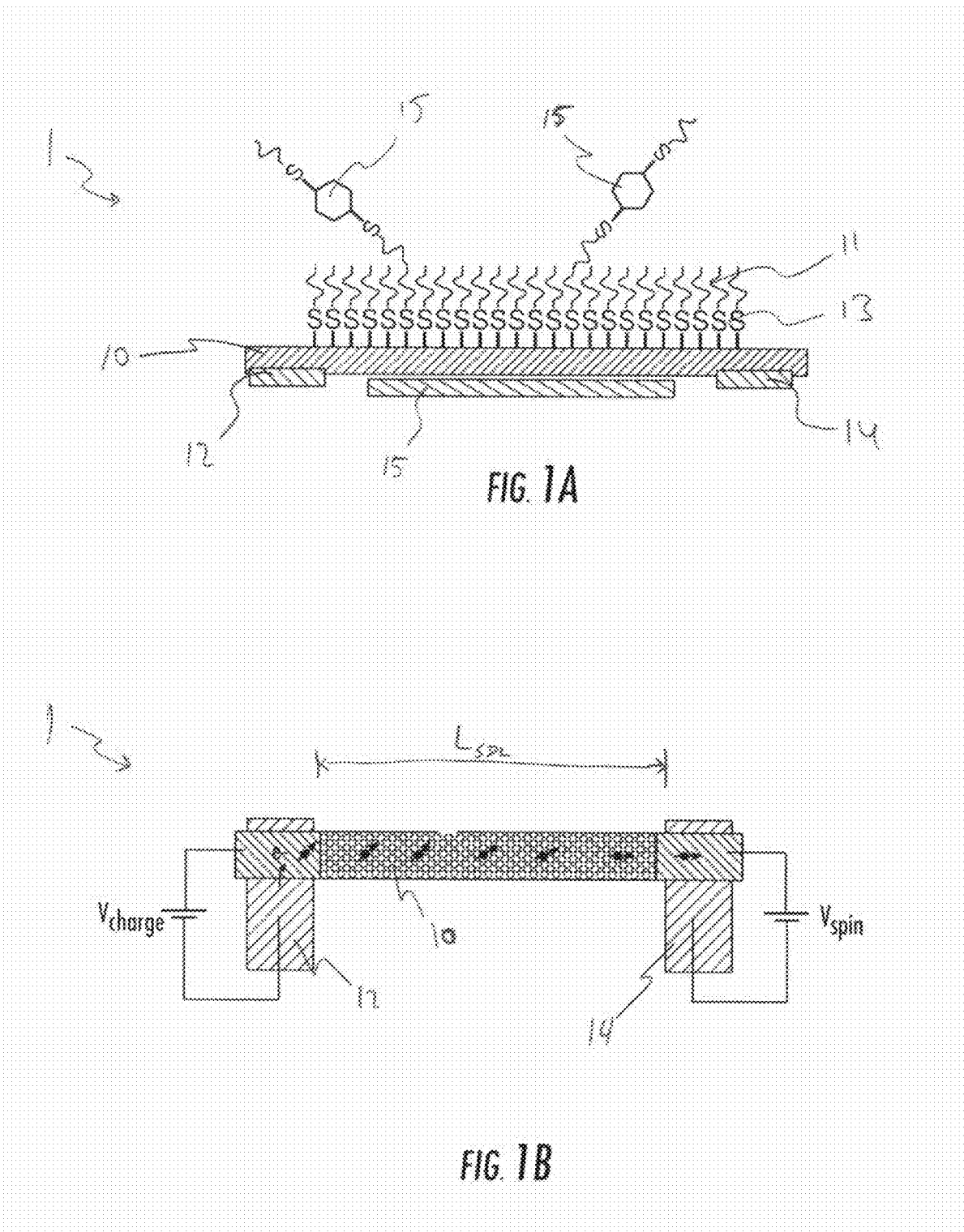
FIGS. 1a and 1b show a schematic of one embodiment of a sensor having a thin bar of an organically capped metal layer patterned on top of ferromagnetic injector and detector films.

Repeat use of reference characters in the present specification and drawings is intended to represent the same or analogous features or elements of the present invention.

DETAILED DESCRIPTION OF INVENTION

It is to be understood by one of ordinary skill in the art that the present discussion is a description of exemplary embodiments only, and is not intended as limiting the broader aspects of the present invention.

The present invention is generally directed to a novel spintronic sensor technology which can be employed as a chemical sensor for chemical detection, a magnetic field sensor for magnetic data storage applications (e.g. mass storage or magnetoresistive random access memory), and as a spin transistor. This invention uses a chemically-controlled magnetic material as a component of a multilayer device together with standard ferromagnetic layers to offer chemical sensitivity, as well as enhanced magnetic sensitivity compared with traditional magnetoresistive sensors.

In one particular embodiment, the bi-layer sensor includes an organically-capped metal (e.g., gold) film which displays permanent magnetism as a system. For example, sulfur atom linkages (i.e., thiol linkages) can be used to bond the organic molecule to the metal film creating a multilayer film (e.g., a bilayer, trilayer, etc.), such as in a thiol self-assembled monolayer or thiol SAM, or polyalinine. However, many other organic structures that exhibit permanent magnetism can also be used to cap the films. Moreover, while gold (Au) is a preferred metal, other metals, such as silver (Ag), aluminum (Al), copper (Cu), platinum (Pt), palladium (Pd), etc., can exhibit similar properties as Au when used in devices of the present invention. In particular, Ag, Al, and Cu all have an odd number of electrons, as does Au. It is proposed by the present invention that these metallic-organic (e.g. Au-thiol) layers be used in conjunction with ferromagnetic thin films as the basis of a novel class of magnetoresistive (spintronic) devices.

In one embodiment of the present invention, an organically capped bilayer film (e.g., Au-thiol) in a spintronic device is used as a spintronic chemical sensor. It has been reported that the magnetic moment in a Au-polyalinine bilayer (with a sulfur, i.e. thiol, linker atom to the Au) decreases with time after being exposed to air. Thus, the present inventors have discovered that the magnetic resistance of the Au-polyalinine bilayer can be used in a chemical sensor to detect the presence of an analyte in the atmosphere. Specifically, any analyte that can attach (e.g., bond) to the organic cap can create a change in the magnetic resistance of the bilayer.

For example, FIG. 1 shows an exemplary schematic of one embodiment of the proposed sensor 1. A thin bar or film 10 of metal (e.g., Au) is patterned on top of ferromagnetic injector film 12 and ferromagnetic detector film 14. These structures are arranged in a geometry which is commonly used to measure spin diffusion. For example, the metal film 10 capped with organic tails 11 attached to the metal 10 through sulfur linkages 13 is positioned over a biasing magnet 15 and between the ferromagnetic injector film 12 and ferromagnetic detector film 14. The metal film 10 capped with organic tails 11 can be referred to as a bilayer film.

A charge current enters the ferromagnet injector 12 and passes to ground through the organically capped metal film 10 through an Ohmic or tunnel contact. The spins of the electrons entering the organically capped film 10 are polarized by passing through the ferromagnetic injector 12. Therefore, while the charge current is returned to ground, there is a characteristic length over which the spins diffuse into the metal film 10, called the spin diffusion length (SDL) shown as $L_{SDL}$ in FIG. 1. In Au, different measurements of the SDL suggest that the SDL ranges from 50-250 nm. This length $L_{SDL}$ sets the active area of the device. If the Au film is shorter than the SDL, then the spins are detected as a spin current in the ferromagnetic detector.

FIGS. 2a-2c show three different types of devices. The first device 2, shown in FIG. 2a, has a metal film 10' without any organic layer (thiol, polyalinine, etc.). The spin current is constant with time for a given charge current. However, if instead of the bare metal film 10', an organically capped metal bilayer 10 (e.g., Au-thiol with polyalinine) is employed, such as in FIG. 2b, and if the system 3 is kept in an inert atmosphere, no spin current will be detected, because the finite magnetization of the organically capped metal bilayer 10 randomizes the spin before it has a chance to diffuse across the region. Once this device is exposed to the atmosphere (as shown in FIG. 2c), an analyte 15 can be attached to the organic tail 11 of the bilayer 10, and the magnetism decreases with time. Thus, the spin diffusion current can be detected again. These three embodiments are shown in the schematic graphs on the right side of the page, where the hypothetical spin current of the three cases is graphed as a function of time. Over time, in the atmospheric embodiment 4, the signal changes as the magnetism is reduced. By modifying the organic tail 11 of the bilayer 10, different sensitivities to different atmospheric chemicals (e.g., analytes 15) can be engineered, which is within the capabilities of one of ordinary skill in the art. As a result, an array of these spintronic devices could be used to sense a multitude of atmospheric chemicals. For example, a device can be engineered having a specific organic tail 11 that has a strong affinity for a particular analyte 15. After the device has been constructed, it can be exposed to the particular analyte 15 to determine the affect such an exposure has on the device. Then, when in use, the sensor can be used to detect the presence of that targeted analyte 15 by monitoring for that particular response predetermined by the control device.

FIG. 3 shows how the resistance of the devices in FIGS. 1-2 changes with an applied magnetic field. The graph on the left shows a hysteretic change in resistance as the spin current is overcome by the applied magnetic field. The graph on the right, where the Au-thiol layer is magnetic, shows no change in resistance. The intermediate states between these two graphs are what this sensor would detect as the Au-thiol magnetism changes.

Figure 4:
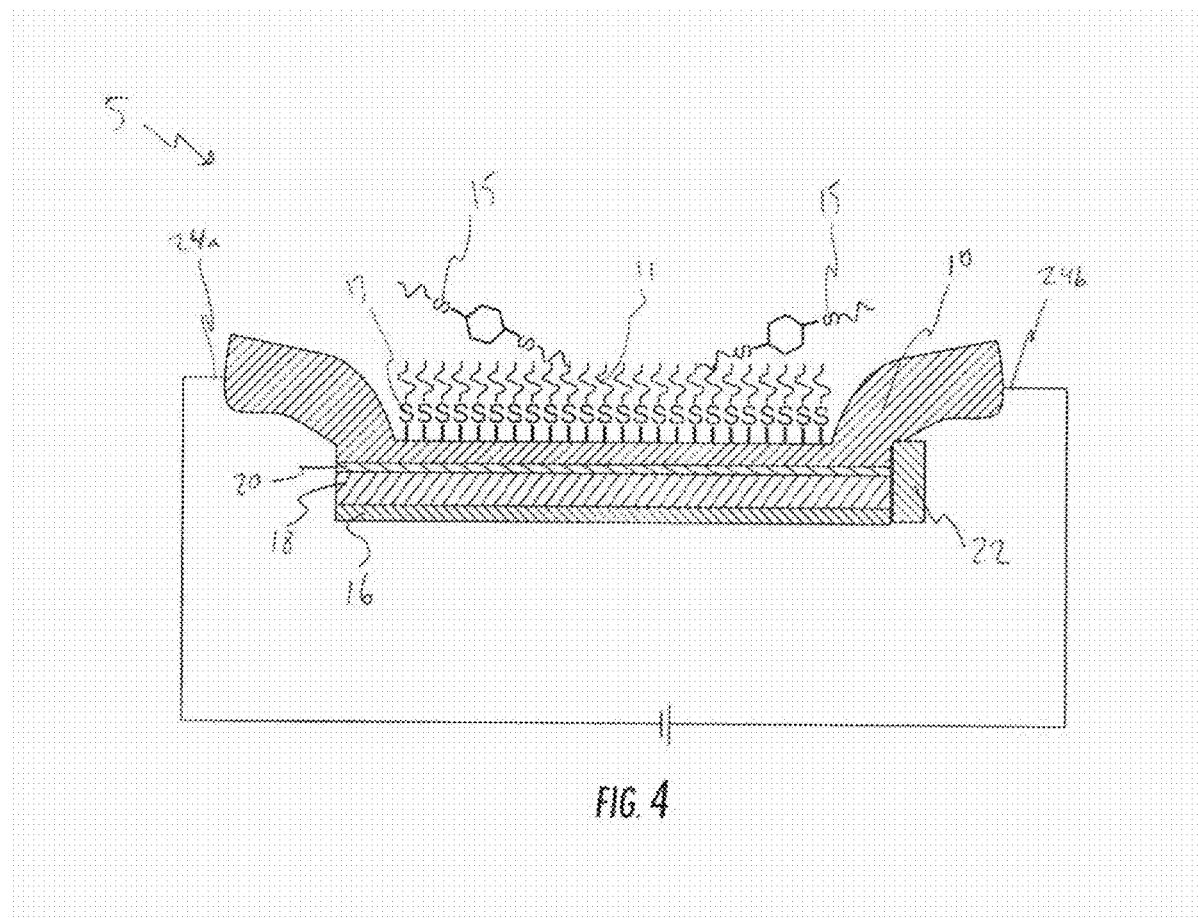
FIG. 4 shows another embodiment of the spintronic chemical sensor.

FIG. 4 shows an alternative embodiment of a spintronic chemical sensor. This device geometry is similar to a current-in-plane (CIP) giant magnetoresistance multilayer or spin valve. Here the multilayer structure 5 has an antiferromagnetic layer 16 (e.g. PtMn or IrMn) to pin the magnetization of a ferromagnetic layer 18 (e.g., CoFe or NiFe alloy). A spacer layer 20 (e.g., Cu) is deposited, and followed finally by the organically capped metal bilayer structure 10. Permanent magnets 22 can be deposited on the sides of the structure 5 to bias the layers into a non-aligned state, and leads 24a, 24b are deposited on the sides such that an electric current flows sideways through the multilayer. The active area (i.e., the organic tails 11) of the device is exposed to the atmosphere, and the magnitude of the observed magnetoresistance will depend on the degree to which the organically capped metal bilayer 10 is magnetic. As the magnetization decreases due to adsorption of atmospheric chemicals (i.e., analytes 15), the magnetoresistance will correspondingly decrease, enabling one to monitor the atmosphere for particular chemical species.

Figure 5:
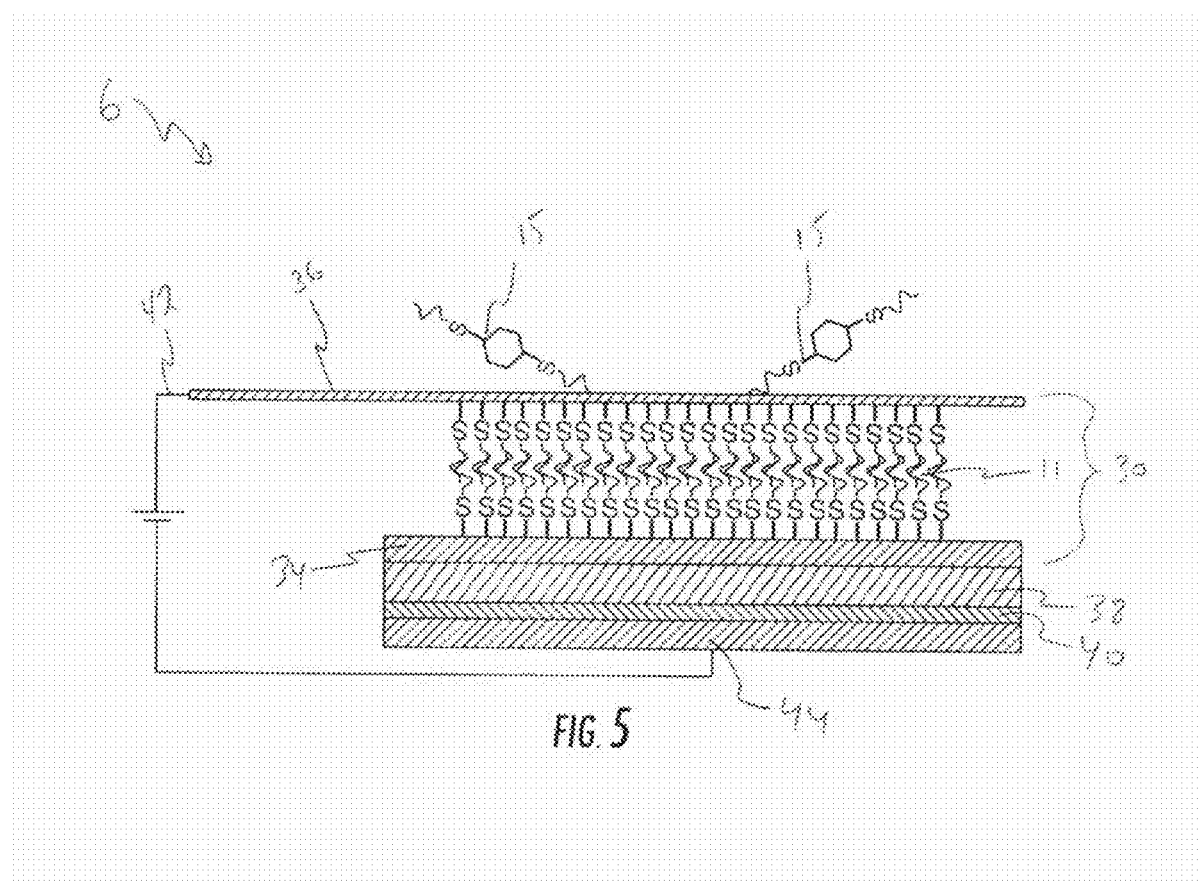
FIG. 5 shows another embodiment of a sensor, this time a magnetic tunnel junction (MTJ) device geometry.

FIG. 5 shows another embodiment of the present invention, this time the sensor device 6 has a magnetic tunnel junction (MTJ) device geometry. Such structures have been demonstrated to have magnetoresistance when used with ferromagnetic electrodes. Here the current flows perpendicular to the plane (CPP). A metal-thiol-metal trilayer (e.g., Au-thiol-Au trilayer), where the sulfurs 13 are located on top 32 of the structure as well as the bottom 34, with the organic tails 11 being the insulating tunnel barrier. The top lead film 36 is extremely thin so as to change its magnetism when atmospheric chemicals adsorb onto the lead. Additionally, a ferromagnetic layer 38 and an antiferromagnetic layer 40 are present. A top lead 42 and a bottom lead 44 supply a current through the system.

Figure 6:
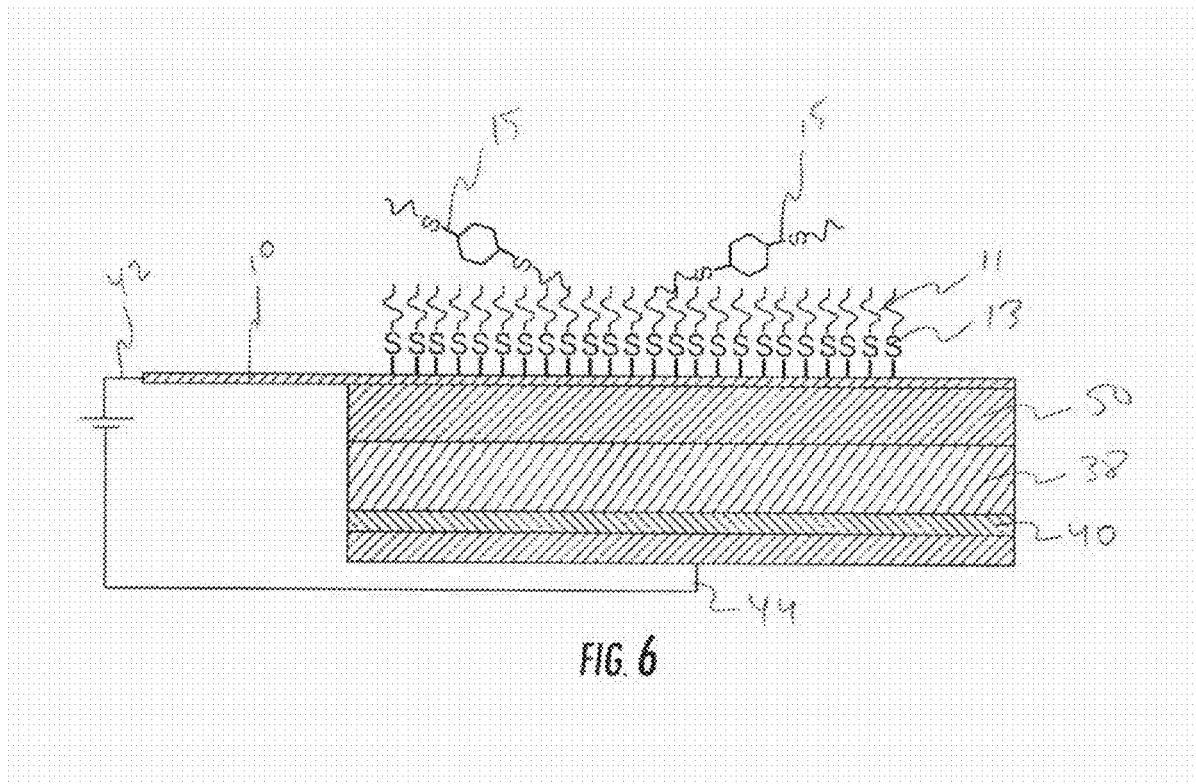
FIG. 6 shows yet another embodiment, wherein instead of using the thiol SAM as the tunnel barrier, a conventional aluminum-oxide ($Al_2O_3$) or MgO or other tunnel barrier is used.

FIG. 6 shows another embodiment of a MTJ device 6', wherein instead of using the thiol SAM as the tunnel barrier, a conventional aluminum-oxide ($Al_2O_3$) or MgO or other tunnel barrier 50 is used, only in this case, the top lead is made of an organically capped metal film 10, i.e. the top electrode is treated with a layer of thiols to facilitate its ability to sense atmospheric chemicals. In this embodiment, it is the current through the top lead whose degree of spin alignment with the pinned ferromagnet determines the resistance of the structure and changes under atmospheric conditions.

Figure 7:
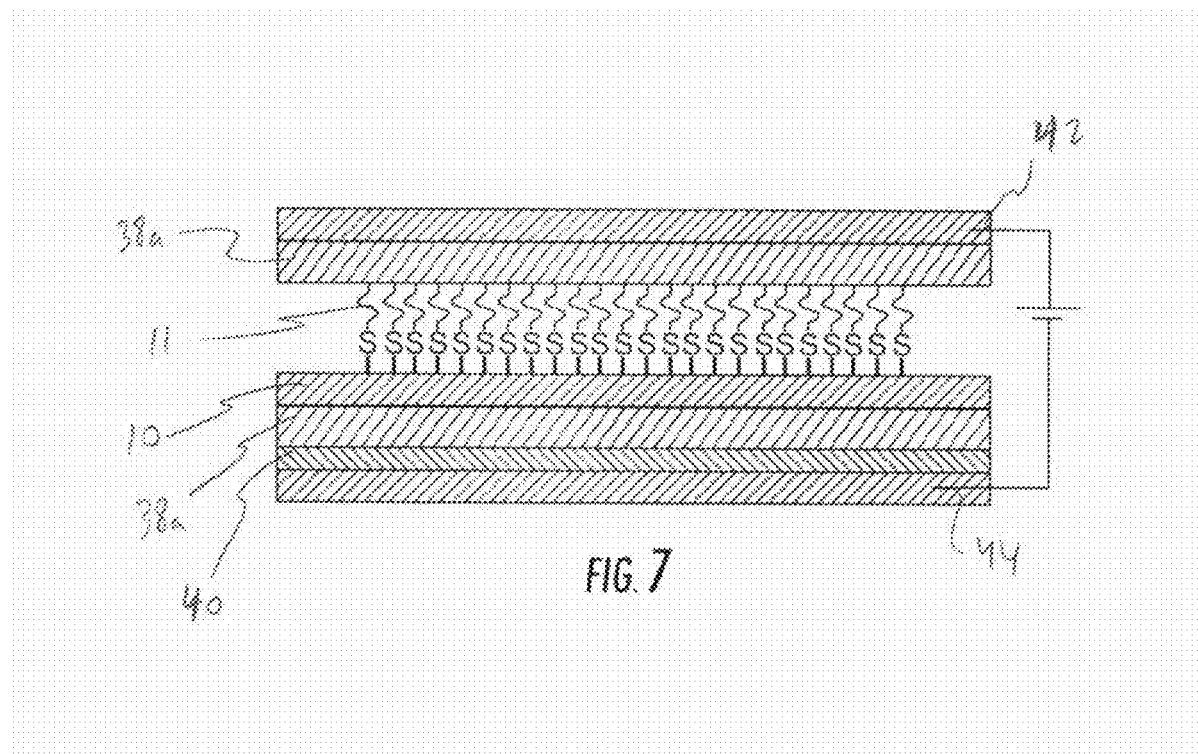
FIG. 7 shows a magnetic tunnel junction sensor employing an organically capped metal layer as a spin dependent tunnel barrier.
Figure 8:
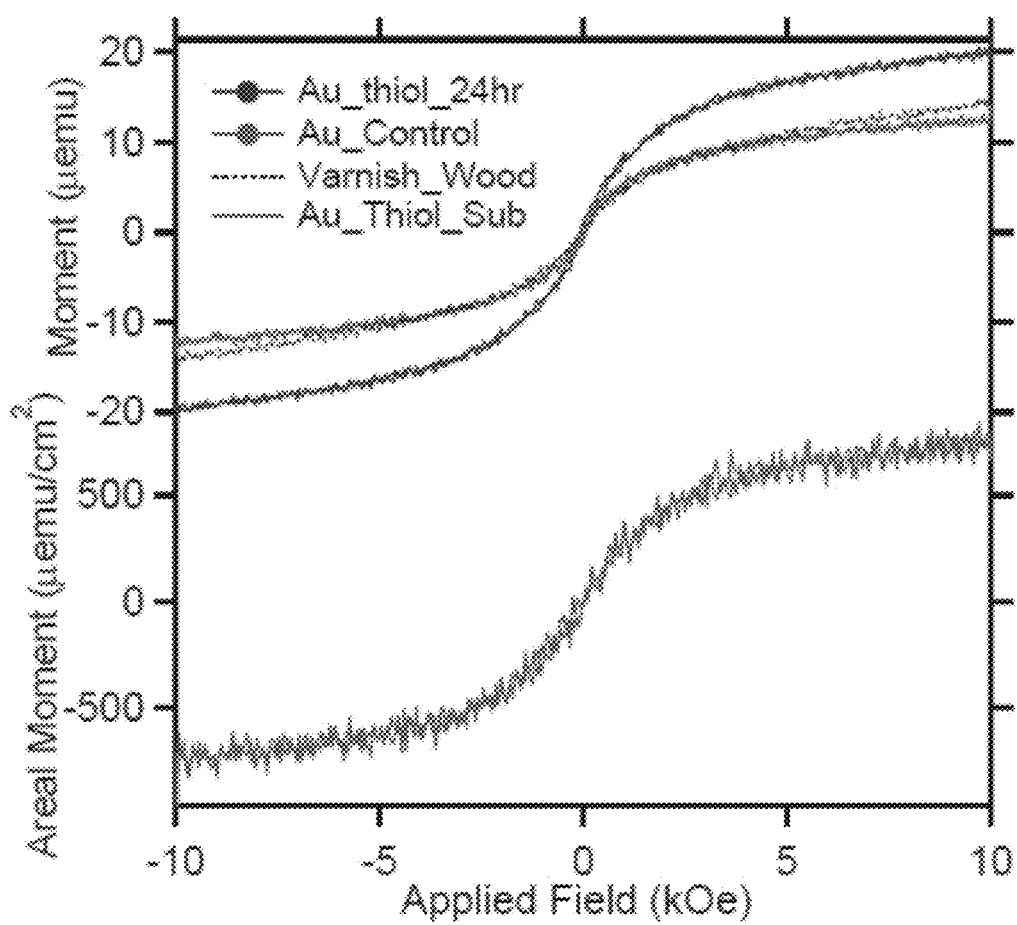
FIG. 8 shows Plot 1 in which the upper graph shows hysteresis loops for Au, Au capped with dodecane thiol (1 mM for 24 hours), and the sample mount (top); and the lower graph is the difference between the Au and Au-thiol loops.
Figure 9:
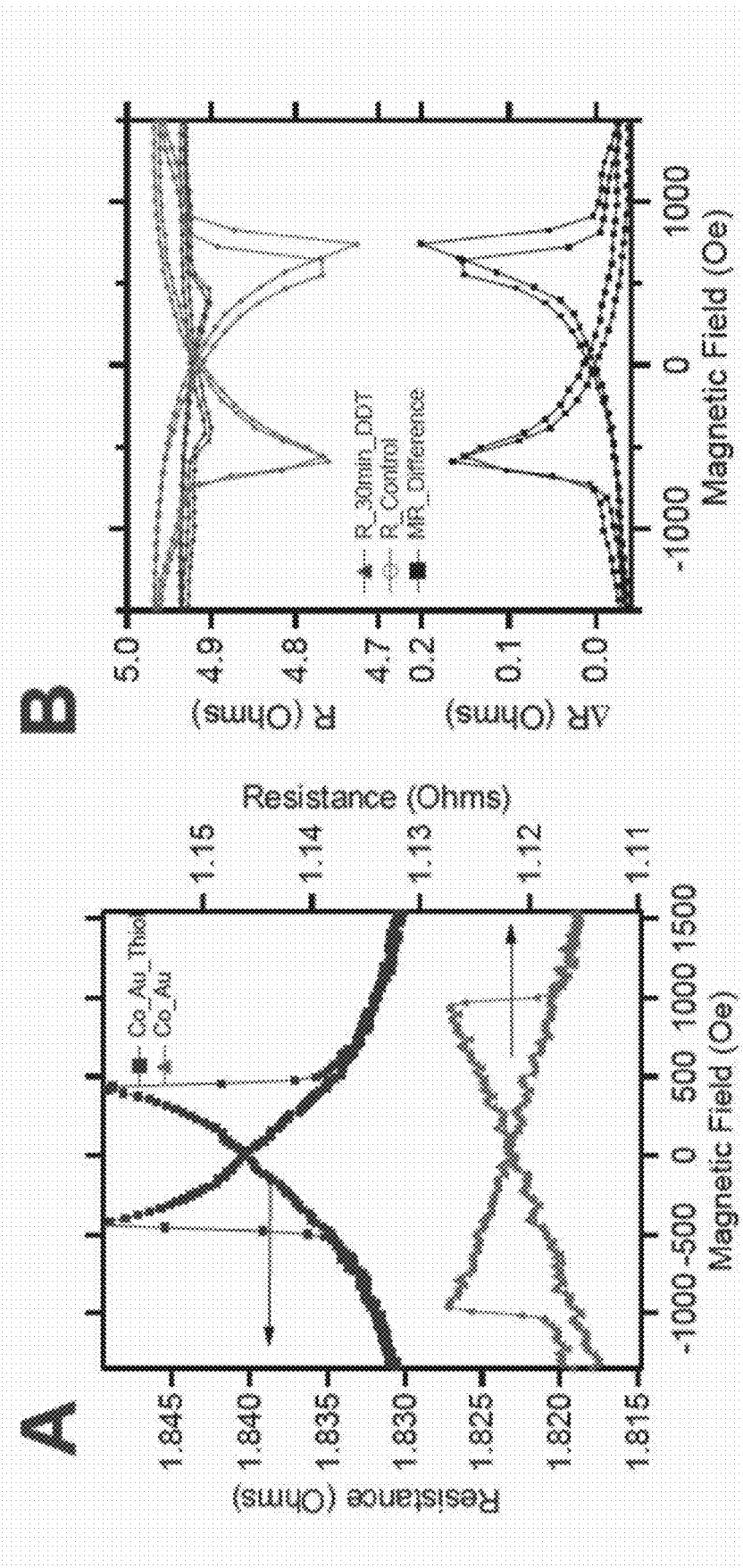
FIG. 9 shows Plot a and b, which show resistance as a function of field for two different Co (20 nm)-Au (5 nm) and Co (20)-Au (5)-thiol (1 mM dodecane for ½ hour) films.

Finally, FIG. 7 shows a magnetic tunnel junction sensor 6" employing an organically capped metal bilayer 10 (e.g., Au-thiol) as a spin dependent tunnel barrier. In FIG. 7, two ferromagnetic layers 38a, 38b are present as well as the organically capped metal layer 10. To the extent that having spin dependent transport through the organically capped metal layer 10 enhances the magnetoresistance, this device could be used as an improved magnetic field sensor, for example, in next generation magnetic random access memory devices or hard disc drives for sensing bit directions via magnetic fields, or in any other magnetoresistive sensor technology. FIG. 7 could be modified to have a single ferromagnet together with the organically capped metal layer 10 instead of two ferromagnetic layers. One skilled in the art would realize that there are numerous other combinations of conventional magnetoresistive device geometries wherein organically capped metal layer 10 magnetic layers could be employed.

The present invention proposes candidate sensor designs for chemical and magnetic field sensing, employing a metallic-organic (eg. Au-thiol) spintronic bilayer as a spin-active electron transport element, which is sensitive to atmospheric conditions and can be chemically adjusted to have different sensitivities to different chemical species. An array of these devices could be fabricated similarly to an MRAM device, but where individual sets of devices would sense a different chemical species. Such a device would be a low power, portable alternative to other proposed atmospheric chemical sensor technologies.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

EXAMPLES

Plot 1 shows preliminary magnetometry data we have taken for a 24 hr Au/dodecanethiol (1 mM in ethanol) film, a Au film control, a sample mount control, and the difference between the Au-thiol and Au control loops. The samples are 1×1 $mm^2$ photolithographically patterned Au squares grown on Si wafers. The observed magnetization is ~7.5×10 −4 $emu/cm^2$ at 1 T, 2.7× lower than the $2×10^{-3}$ $emu/cm^2$ observed by Hernando et al. for Lewis conjugate on glass, but 8× larger than the $9.33×10^{-5}$ $emu/cm^2$ found by for polyalanine on glass. Taken together, these results display three different magnetizations for three different Au—S chemistries. However, achieving reproducibility has been challenging. We have fabricated samples which, while showing weaker moments, display increasing moment with immersion time. Other samples display para- and diamagnetic moments near the sensitivity limit of magnetization values highlights the need for meticulous control during sample fabrication, with a focus on which process variables directly influence the Au-thiol moment. For example, Au hydrophilicity and cleanliness, as well as the Au crystalline texture and roughness may strongly affect the magnetization.

Plot 1—The upper graph shows hysteresis loops for Au, Au capped with dodecane thiol (1 mM for 24 hours), and the sample mount (top). The lower graph is the difference between the Au and Au-thiol loops.

An example of MR detection of Au-thiol magnetism is shown in plots 2A-B, where the resistance of two different Co/Au (red) and Co/Au/thiol (blue) thin films is plotted as of our vibrating sample magnetometer (VSM), i.e. much weaker magnetization. The wide range a function of perpendicular field. In both cases the two curves have different transition fields for the in-plane MR component (features between +/−1000 Oe), and a 30 minute immersion in 1 mM dodecane thiol modifies the field necessary to observe the in-plane transitions in the Co films by 500 and 2000e for Plots 2A and 2B respectively. Repeated experiments show similar shifts of varying sizes, and an immersion in pure ethanol shows no shift within experimental error. We have observed subtractive and additive field shifts, as well as an asymmetry in the field shift rate as a function of sample angle relative to the applied field. Au-thiol magnetism appears to modify the magnetotransport in Co films by producing a bias field which either opposes or assists the applied field. This shift changes with time after immersion, suggesting that the thiol SAM evolves with time.

Plot 2a and 2b—Resistance as a function of field for two different Co (20 nm)-Au (5 nm) and Co (20)-Au (5)-thiol (1 mM dodecane for ½ hour) films. The peaks are the in-plane AMR response for out-of-plane fields which are not perfectly normal to the film plane. The adsorption of thiol shifts these peaks to lower fields in these cases, along with other changes.

Those of ordinary skill in the art will understand that the devices disclosed and described herein are meant only as examples and are not intended to limit the scope of the invention.

The invention claimed is:

1. A method of detecting an analyte, wherein the method comprises:
   (a) applying an electric current to a multilayer sensor, wherein the multilayer sensor comprises:
      a multilayer film having an organic layer on a metal film, wherein the multilayer sensor displays permanent magnetism, and wherein the organic layer is positioned on the spintronic chemical sensor such that the analyte, when present, attaches to the organic layer; and
      a ferromagnet configured to provide a current to the multilayer film; and
      a ferromagnet detector positioned opposite of the ferromagnet; and
   (b) measuring any change in resistance of the electronic current through the multilayer sensor to determine the presence of the analyte.

2. A method of detecting an analyte, wherein the method comprises:
   (a) applying an electric current to the multilayer sensor through leads attached to each end of the sensor, wherein the multilayer sensor comprises:
      a multilayer film having an organic layer on a metal film, wherein the multilayer sensor displays permanent magnetism, and wherein the organic layer is positioned on the spintronic chemical sensor such that the analyte, when present, attaches to the organic layer; and
      a ferromagnet configured to provide a current to the multilayer film; and
      a ferromagnet detector positioned opposite of the ferromagnet; and
   (b) measuring any change in magnetoresistance of the electronic current through the multilayer sensor to determine the presence of the analyte.

3. The method as in claim 1, wherein the organic layer is bonded to the metal film via a thiol linkage.

4. The method as in claim 1, wherein the organic layer comprises a polyalinine.

5. The method as in claim 1, wherein the metal film comprises gold.

6. The method as in claim 1, wherein the metal film comprises silver.

7. The method as in claim 2, wherein the organic layer is bonded to the metal film via a thiol linkage.

8. The method as in claim 2, wherein the organic layer comprises a polyalinine.

9. The method as in claim 2, wherein the metal film comprises gold.

10. The method as in claim 2, wherein the metal film comprises silver.

* * * * *